United States Patent
Schabbach et al.

(10) Patent No.: US 11,504,480 B2
(45) Date of Patent: Nov. 22, 2022

(54) DATA COLLECTION FROM A MEDICAMENT DELIVERY DEVICE

(71) Applicant: Sanofi-Aventis Deutschland GMBH, Frankfurt am Main (DE)

(72) Inventors: Michael Schabbach, Frankfurt am Main (DE); Beate Franke, Frankfurt am Main (DE)

(73) Assignee: Sanofi-Aventis Deutschland GMBH

( * ) Notice: Subject to any disclaimer, the term of this patent is extended or adjusted under 35 U.S.C. 154(b) by 696 days.

(21) Appl. No.: 16/468,184

(22) PCT Filed: Dec. 12, 2017

(86) PCT No.: PCT/EP2017/082311
§ 371 (c)(1),
(2) Date: Jun. 10, 2019

(87) PCT Pub. No.: WO2018/108855
PCT Pub. Date: Jun. 21, 2018

(65) Prior Publication Data
US 2019/0328979 A1 Oct. 31, 2019

(30) Foreign Application Priority Data
Dec. 13, 2016 (EP) .................................. 16203824

(51) Int. Cl.
*A61M 5/315* (2006.01)
*G16H 20/17* (2018.01)
(Continued)

(52) U.S. Cl.
CPC .... *A61M 5/31568* (2013.01); *A61M 5/31553* (2013.01); *G06V 10/17* (2022.01);
(Continued)

(58) Field of Classification Search
None
See application file for complete search history.

(56) References Cited

U.S. PATENT DOCUMENTS

| 5,651,775 A | 7/1997 | Walker et al. |
| 6,482,185 B1 | 11/2002 | Hartmann |

(Continued)

FOREIGN PATENT DOCUMENTS

| CN | 106102593 | 11/2016 |
| EP | 3042676 | 7/2016 |

(Continued)

OTHER PUBLICATIONS

PCT International Preliminary Report on Patentability in International Appln. No. PCT/EP2017/082311, dated Jun. 18, 2019, 7 pages.
PCT International Search Report and Written Opinion in International Appln. No. PCT/EP2017/082311, dated Mar. 14, 2018, 9 pages.

*Primary Examiner* — Manuel A Mendez
(74) *Attorney, Agent, or Firm* — Fish & Richardson P.C.

(57) ABSTRACT

A data collection apparatus comprises a camera configured to obtain first and second recordings of at least a portion of a medicament delivery device, said portion including a first component and a second component, the first component being configured to move relative to the second component as medicament is expelled from the medicament delivery device. The data collection apparatus also comprises a processing arrangement configured to determine, from said first and second recordings, positions in the first and second recordings of the first component relative to the second component, and determine an amount of medicament that has been expelled by the medicament delivery device by comparing the position, in the first recording, of the first
(Continued)

component relative to the second component with a position, in the second recording, of the first component relative to the second component.

20 Claims, 9 Drawing Sheets

(51) Int. Cl.
*G06V 10/10* (2022.01)
*G06V 10/20* (2022.01)
*G06V 10/75* (2022.01)
*G06T 7/70* (2017.01)
*G16H 10/60* (2018.01)
*A61M 5/31* (2006.01)
*G06V 20/40* (2022.01)

(52) U.S. Cl.
CPC .......... *G06V 10/255* (2022.01); *G06V 10/758* (2022.01); *G16H 20/17* (2018.01); *A61M 2005/3126* (2013.01); *A61M 2205/3306* (2013.01); *A61M 2205/3584* (2013.01); *A61M 2205/505* (2013.01); *A61M 2205/52* (2013.01); *G06T 7/70* (2017.01); *G06T 2207/10016* (2013.01); *G06V 20/48* (2022.01); *G06V 2201/034* (2022.01); *G16H 10/60* (2018.01)

(56) References Cited

U.S. PATENT DOCUMENTS

| | | | |
|---|---|---|---|
| 2006/0178578 A1 | 8/2006 | Tribble et al. | |
| 2008/0243088 A1 | 10/2008 | Evans | |
| 2009/0082737 A1* | 3/2009 | Bobst | A61M 5/5086 604/218 |
| 2011/0144616 A1* | 6/2011 | Michaud | A61M 5/31513 604/153 |
| 2012/0197184 A1* | 8/2012 | Okuda | A61J 1/2096 141/2 |
| 2014/0357304 A1 | 12/2014 | Ostrander et al. | |
| 2015/0209114 A1 | 7/2015 | Burkholz et al. | |
| 2015/0224265 A1* | 8/2015 | Jugl | A61M 5/31515 33/517 |
| 2016/0038685 A1 | 2/2016 | Hunkeler et al. | |
| 2016/0074587 A1 | 3/2016 | Searle et al. | |

FOREIGN PATENT DOCUMENTS

| | | |
|---|---|---|
| JP | 2007-207085 | 8/2007 |
| JP | 2014-528812 | 10/2014 |
| WO | WO 2013/053695 | 4/2013 |
| WO | WO 2015/116805 | 8/2015 |
| WO | WO 2016/062605 | 4/2016 |
| WO | WO 2016/131973 | 8/2016 |
| WO | WO 2018/108855 | 6/2018 |

* cited by examiner

DATA COLLECTION FROM A MEDICAMENT DELIVERY DEVICE

CROSS REFERENCE TO RELATED APPLICATIONS

The present application is the national stage entry of International Patent Application No. PCT/EP2017/082311, filed on Dec. 12, 2017, and claims priority to Application No. EP 16203824.4, filed on Dec. 13, 2016, the disclosures of which are incorporated herein by reference.

TECHNICAL FIELD

The present disclosure relates to collecting data from a medicament delivery device by detecting changes in its status, for example to determine an amount of a medicament delivered to a user.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor medicaments administered by a patient, it is desirable to measure information related to a condition and/or use of the injection device, for example, one or more of the injected insulin type, dose and timing of the injection, in a manner that is reliable and accurate. In particular, a patient suffering from a chronic medical condition requiring regular doses of medicament may need to adjust the administered dosage amounts frequently. Such adjustments to the doses may be determined based on information regarding recently administered dosage amounts and in the context of other information relevant to the patient's condition, such as their food intake, physical activity, certain biomarkers such as blood glucose level, and so on.

SUMMARY

According to a first aspect, a method of collecting data from a medicament delivery device includes obtaining a first recording of at least a portion of a medicament delivery device using a camera, said portion including a first component configured to, as medicament is expelled from the medicament delivery device, move relative to a second component of the medicament device and determining, from said first recording, at least a position of the first component relative to said second component. The recording may comprise at least one image, e.g. a photograph or series of images, e.g. a video recording or video stream.

For example, the first component may be a piston in a medicament container of the medicament delivery device, or a dosage knob that rotates as medicament is expelled.

The method may include, based on said first recording, determining information regarding one or more of the medicament and the medicament delivery device provided in attributes provided on said portion.

The method may include determining an amount of medicament that has been expelled based at least in part on determining the position of said first component in said first recording. Determining the amount of medicament that has been expelled may include comparing the position of the first component in said first recording with a position of said first component in a second recording of said portion captured previously or subsequently to the first recording. For example, recordings of the component before and after the medicament is expelled may be compared. The medicament dosage amount may be determined based on the position of the first component and stored information regarding the position of the first component or expelled medicament amounts determined previously.

Where first and second recordings are utilized, the obtaining of the first and second recordings may be performed by capturing two photographs and/or by capturing a video and selecting two images from the video stream as first and second images, respectively. Analysis may provide determine a position of a first component. Where video recording is used, multiple second recordings may be obtained and analyzed, allowing repeated position determinations to be made. Such multiple recordings may allow for statistical evaluation when determining the position of the first component. An increased number of recordings may, therefore, allow the position to be determined with increased reliability, even where the resolution of video recordings is lower than the resolution of still recordings.

The method may include statistical algorithms to determine a corrected image from a video e.g. a random sample consensus algorithm. The corrected image may be corrected for skew, pin-cushion distortion, barrel distortion, etc.

A video stream that undergoes the statistical evaluation can comprise at least 50 images. Recording a video at 30 frames per second (fps) can last between 2 and 7 seconds. Optimal results may be obtained with a video stream comprising a number of images in the range of about 70 to about 130. Other frame rates, i.e. the number of images taken per second (or fps) may also be used. According to one embodiment, optimal results may be achieved with a video stream of about 1.5 sec length taken at 60 fps providing about 100 images.

The method may include analysis of attributes provided on the medicament delivery device shown in at least one of the first and second recordings, to identify the particular medicament device and/or the medicament it contains. Information obtained using the attributes may be compared with reference or previously stored information. For example, a check may be made that includes one or more of the following: a check that the correct medicament is being administered, a check to identify the medicament delivery device and prevent a user administering an injection using the wrong device, or a device belonging to another user, and a check that the medicament has not yet expired.

Instructions may be provided to guide positioning of the medicament delivery device relative to the camera. For instance, the method may include, prior to obtaining the first recording, capturing a preliminary recording or recordings using said camera, determining, based on said preliminary recording or recordings, whether the medicament delivery device is positioned to locate the first component in a particular region of the field of view of the camera with a predetermined orientation, if it is determined that the medicament delivery device is not positioned to locate the component in said particular region with the predetermined orientation, determining one or more adjustments to be made to reposition of the medical delivery device relative to the camera and displaying instructions to reposition the medicament delivery device relative to the camera based on the determined adjustments. In one example, the preliminary recording or recordings are captured in a video recording, which is displayed as a "live view", with instructions for adjustments to the position and orientation of the medicament delivery device relative to the camera to guide the user.

Furthermore, the capture of the first recording may be triggered automatically in response to a determination that the medicament delivery device is positioned to locate the component in said particular region with the predetermined orientation. The determination of whether the medicament delivery device is positioned with the predetermined orientation may include analysis of one or more of a brightness profile of pixels in the preliminary recording, positions of features of the medicament delivery device in the preliminary recording, and shapes of features of the medicament delivery device in a recording captured by the camera.

The method may include receiving input information from a user relating to their medical condition and/or activities. Such information may be stored with the medicament dosage information, so that a treatment history indicated by the medicament dosage information may be reviewed by a patient or medical professional in context.

The above aspect also provides a computer program comprising computer-readable instructions that, when executed by a processing arrangement, causes said processing arrangement to perform one of the above methods. For example, the computer program may be provided in an "app" for execution by a smartphone. This can allow data collection to be performed without requiring the manufacture and use of a dedicated device. Also, since a patient may be familiar with a smartphone and, therefore, comfortable handling and operating it, patient compliance with procedures for recording their treatment may be improved.

According to another aspect, a data collection apparatus includes a camera configured to obtain a first recording of at least a portion of a medicament delivery device using a camera, said portion including a first component that moves relative to a second component as medicament is expelled from the medicament delivery device, and a processing arrangement configured to determine, from said first recording, at least a position of the first component relative to the second component.

The processing arrangement may be configured to determine an amount of medicament that has been expelled based at least in part on the position of said first component in said first recording. The processing arrangement may be configured to compare the position of the component in said first recording with a position of said first component in a second recording of said portion, the first recording and the second recording having been captured at different times.

The apparatus may include an output arrangement, such as a display, and be configured to, prior to capturing the first recording, capture a preliminary recording using said camera, using said processing arrangement, determine whether the medicament delivery device is positioned to locate the first component in a particular region of the field of view of the camera with a predetermined orientation based on the preliminary recording, if it is determined that the medicament delivery device is not positioned to locate the component in said particular region with the predetermined orientation, determine one or more adjustments to be made to reposition of the medical delivery device relative to the camera, and, using the output arrangement, present instructions to reposition the medicament delivery device relative to the camera based on the determined adjustments. The processing arrangement may also be configured to trigger the camera to capture the first recording in response to a determination that the medicament delivery device is positioned to locate the first component in said particular region with the predetermined orientation.

The processing arrangement is configured to determine whether the medicament delivery device is positioned with the predetermined orientation by being configured to: analyse brightness profile of pixels in the preliminary recording; analyse positions of features of the medicament delivery device in the preliminary recording; and analyse shapes of features of the medicament delivery device (1) in the preliminary recording.

The apparatus may include an input arrangement configured to receive input information from a user relating to their medical condition and/or activities, wherein the processing arrangement is configured to calculate a medicament dosage amount to be administered in a subsequent medicament delivery based on the determined dosage amount and said input information.

The apparatus may be in the form of a portable computing device, such as smartphone, tablet computer or wearable computer. Where the apparatus is a smartphone, computer readable instructions for controlling the processing arrangement to obtain and process the recordings may be provided in the form of a software application, such as an "app".

BRIEF DESCRIPTION OF THE FIGURES

Example embodiments of the invention will now be described with reference to the accompanying figures, of which.

DETAILED DESCRIPTION

In the following, example embodiments of the present invention will be described with reference to an insulin injection device. The present invention is however not limited to such application and, as noted herein above, may equally well be deployed with injection devices that eject other medicaments, with other types of medical devices.

Figure 1:
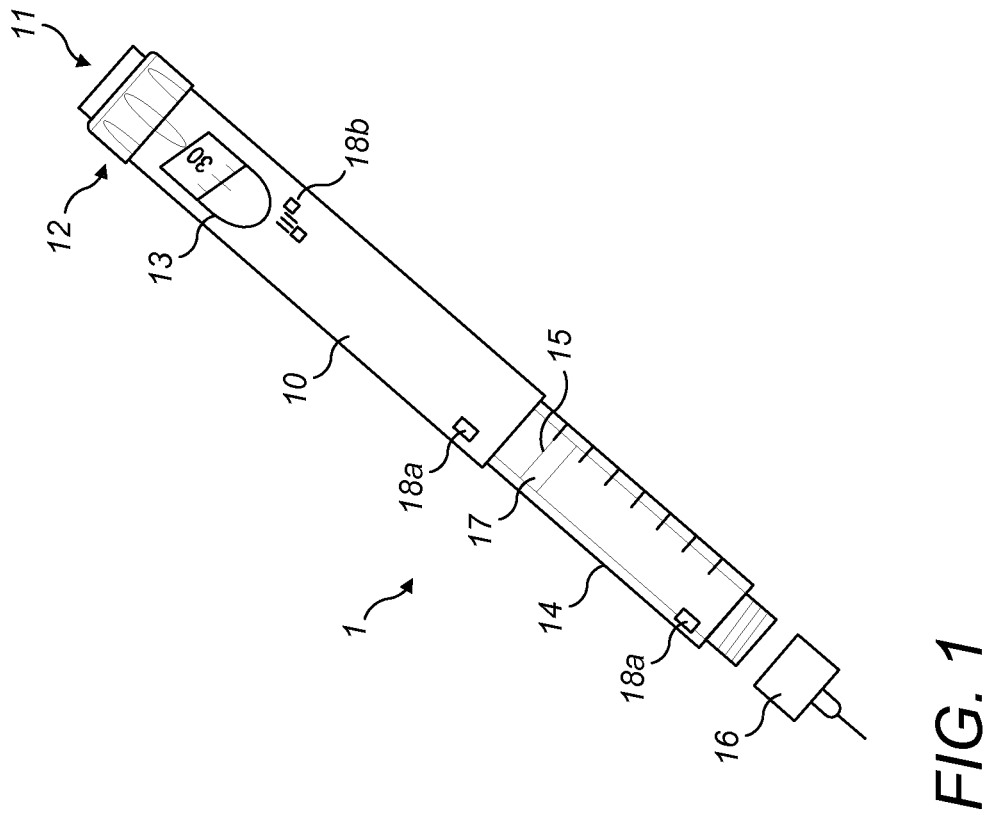
FIG. 1 shows an exploded view of an example medicament delivery device and a data collection apparatus according to a first embodiment.
Figure 1:
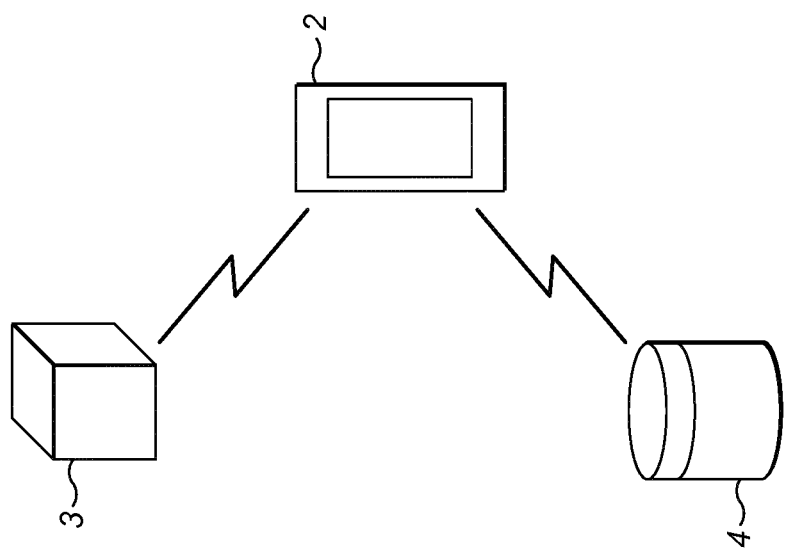

FIG. 1 depicts a medicament delivery device 1 and a data collection apparatus 2 to be used to collect information from the medicament delivery device 1, including medicament dosage amounts administered using the medicament delivery device 1. In some implementations, the data collection apparatus 2 transmits data to a server 3 and/or remote storage 4. For example, the data collection apparatus 2 may transmit data to a cloud storage facility.

In this particular example, the medicament delivery device 1 is a pre-filled, disposable injection pen. Examples of such injection pens include the Sanofi Solostar®, Lantus® and Tujeo® pens.

The medicament delivery device 1 includes a housing 10 having a chamber 14, in which a medicament container 15 is provided. At least a part of the chamber 14 is transparent or translucent, so that at least a portion of the container 15 can be viewed by a user of the medicament delivery device 1. The chamber 14 may be, for example, a polycarbonate material, while the medicament container 15 may be formed of glass.

A medicament dose to be ejected from medicament delivery device 1 can be programmed by the user turning a dosage knob 12. The programmed dose is then displayed via dosage window 13, for instance in multiples of units. In this particular example, the units are so-called International Units (IU), wherein one IU is the biological equivalent of about 45.5 micrograms of pure crystalline insulin (1/22 mg). It should be noted that the programmed dose may equally well be displayed in a different manner.

Figure 2A:
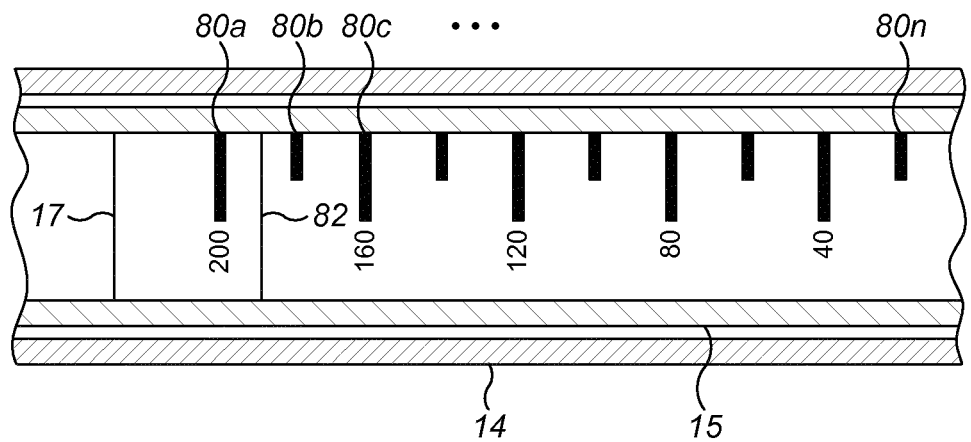
FIG. 2a shows an enlarged view of a medicament chamber in the medicament delivery device shown in FIG. 1 before a first use.
Figure 2B:
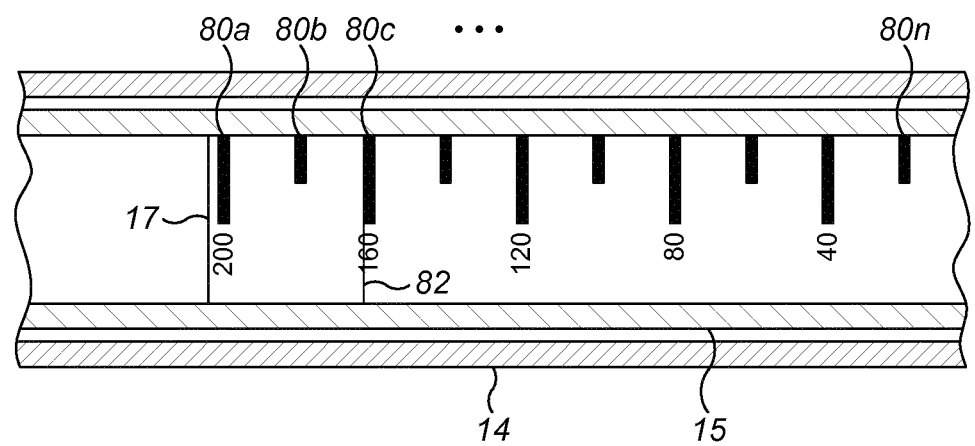
FIG. 2b shows an enlarged view of the medicament chamber shown in FIG. 2a after an amount of medicament has been expelled.

When an injection button 11 is pushed, an amount of medicament corresponding to the medicament dose displayed in the dosage window 13 is ejected from medicament delivery device 1 through the needle 16, through the movement of a piston 17 within the container 15. Before a first use of the medicament delivery device 1, the piston 17 is located at a first position as shown in FIG. 2a. As medicament is expelled from the container 14, the piston 17 moves towards an end of the container 14 that is proximal to the needle 16. FIG. 2b depicts the piston 17 after the first use of the medicament delivery device 1, showing a change in its position within the container 14.

The medicament delivery device 1 shown in FIG. 1 may be used for several injection processes until either the container 14 is empty or an expiration date of the medicament, for example 28 days after the first use of the medicament delivery device 1, is reached.

One or more visual attributes 18a, 18b, 18c are provided on the medicament delivery device 1. The visual attributes 18a, 18b, 18c may include an attribute or a combination of attributes that is unique to the medicament delivery device 1, which can serve to identify the medicament delivery device 1. Alternatively, or additionally, the visual attributes may include an attribute or combination of attributes that provides information identifying the medicament in the container 15 and/or other information such as medicament concentration, medicament expiry date, the model of the medicament delivery device 11 and so on. The visual attributes 18a, 18b, 18c may be in the form of marks, characters, patterns, colours used on part or all of the housing 10, shapes and/or colours of markings on the chamber 14, container 15 or other parts of the housing, or a combination of two or more of such forms. For example, the visual attributes may include a barcode, QR code or the like and/or the shape of tick marks on the medicament container 15.

Figure 3:
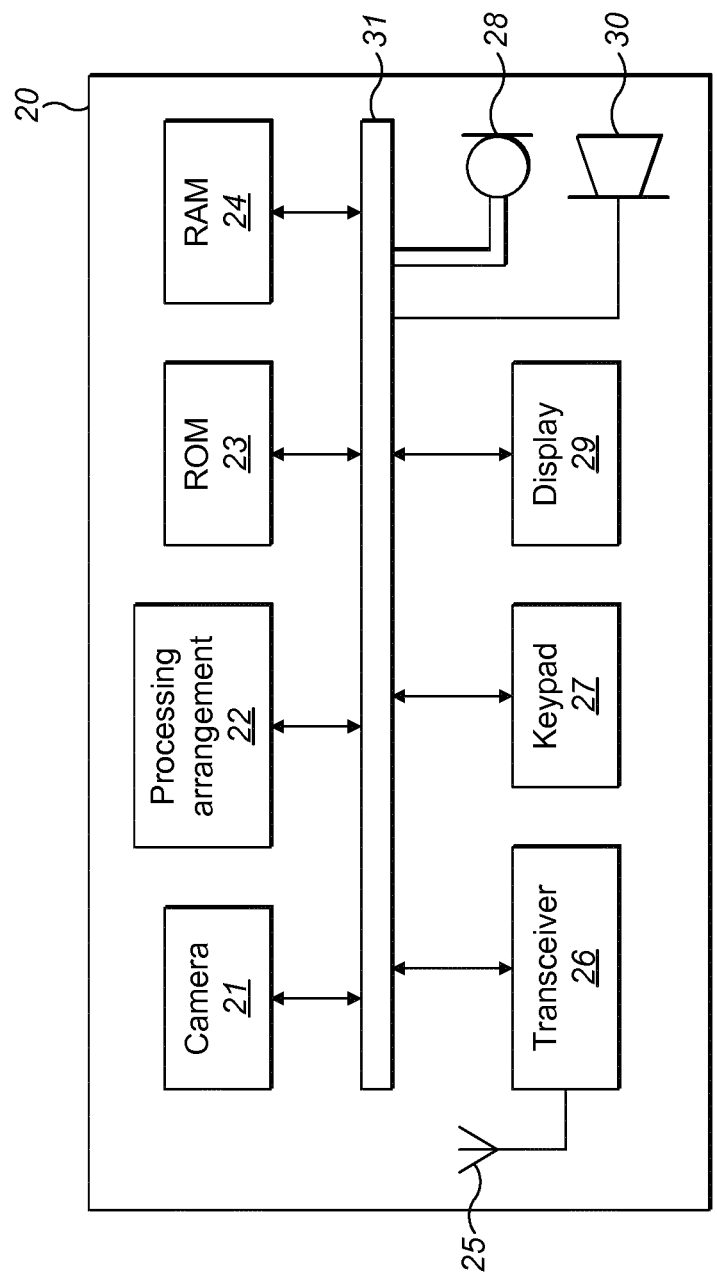
FIG. 3 is a block diagram of the data collection apparatus shown in FIG. 1.

FIG. 3 is a block diagram of the data collection device 12 shown in FIG. 1. In the particular example shown in FIG. 3, the data collection device is a cellphone 20, or "smartphone", equipped with a built-in camera 21, and a processing arrangement 22 including one or more processors or microprocessors, a Digital Signal Processor (DSP), Application Specific Integrated Circuit (ASIC), Field Programmable Gate Array (FPGA) or the like. The camera 21 is configured to capture still recordings and/or video.

The cellphone 20 also includes memory units 23, 24, including a read-only memory 23 and a random access memory 24, which can store software for execution by the processing arrangement 22.

The cellphone 20 also includes communications equipment 25, 26, such as an antenna 25 and a transceiver 26, to permit bi-directional communication with one or more of a cellphone network, a personal area network, a local wireless network and the Internet.

The cellphone 20 further includes an input arrangement 27, 28, such as a keypad 27 and microphone 28, and an output arrangement 29, 30, such as a display 29 and a speaker 30. In some embodiments, the input arrangement 27, 28 may include provide a keypad 27 in the form of part of a touch-screen that utilises some or all of the display 29. The cellphone 20 also includes a communications bus 31 allowing for communication between the camera 21, processing arrangement 22, memory units 23, 24, communications equipment 25, 26, input arrangement 27, 28 and output arrangement 29, 30.

In this particular example, the software stored in the memory units 23, 24 of the cellphone 20 includes an "app" that, when executed by the processing arrangement 22, causes the cellphone 20 to take an recording of the medicament delivery device 11 and process the recording to obtain data the medicament dosage amount and, optionally, other medicament information.

Figure 4:
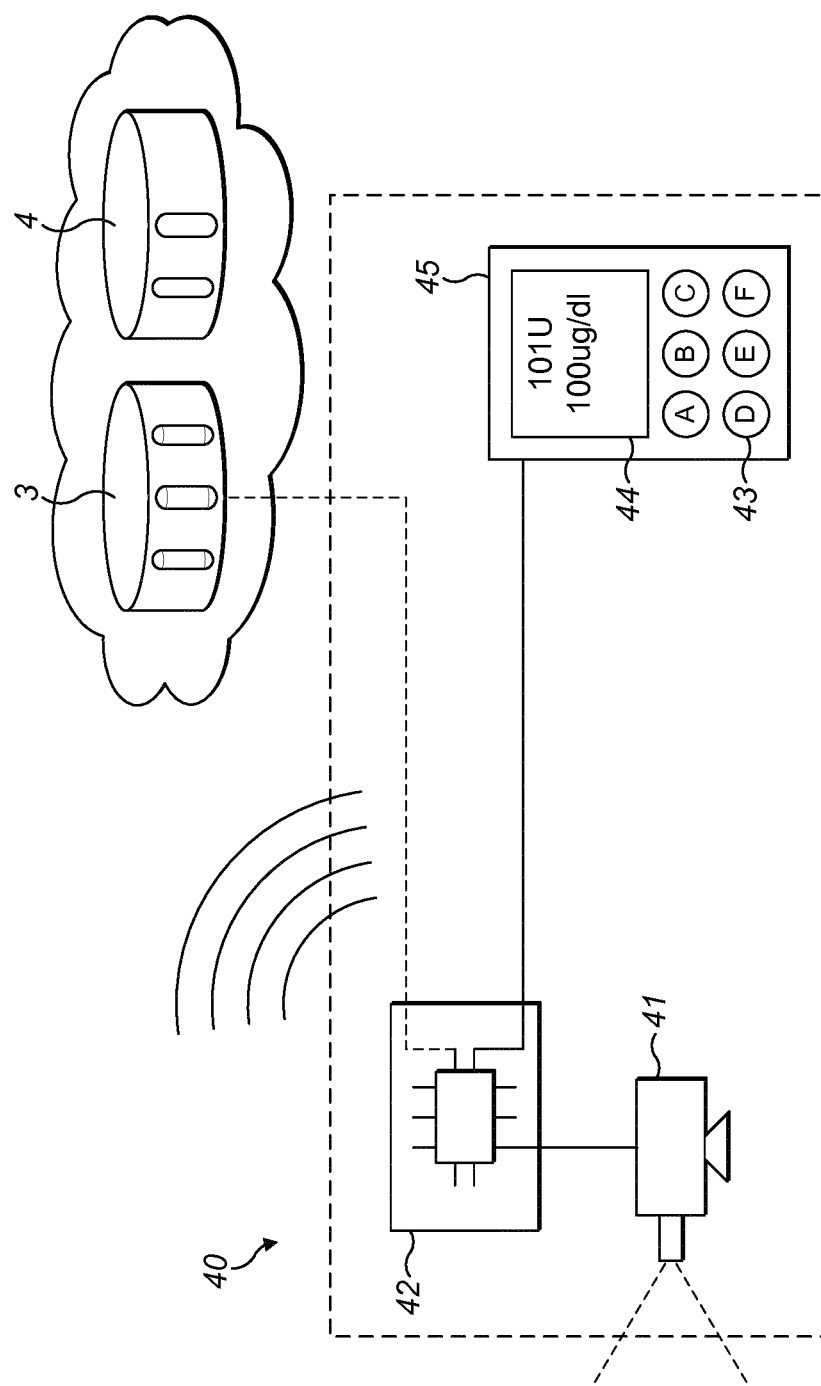
FIG. 4 depicts a data collection apparatus according to another embodiment.

The example data collection apparatus 20 shown in FIG. 3 is a single device configured to capture still and/or video recordings through the camera 21, process the recordings using the processing arrangement 22, receive user input through input arrangement 27, 28 and provide output to the user using output arrangement 29, 30, as well as being able to transmit data to other locations using the communications equipment 25, 26. However, according to another embodiment of the invention, the data collection apparatus may be configured in the form of two or more separate devices. For example, as shown in FIG. 4, in a data collection apparatus 40 according to another embodiment, a stand-alone camera device 141 may be provided to capture recordings and transmit them to a separate data processing device 142 for analysis. Alternatively, or additionally, an input arrangement, such as a keyboard 43, and an output arrangement, such as a display 44, may be provided by a separate interface device 145 that is in communication with the data processing device 142.

In yet another example embodiment, not shown, the data collection apparatus may include a wearable computer that includes a camera device and, optionally, one or more of a data processing device and an interface device. For example, where a camera is provided in a computing device that is worn on the user's head, it may be easier for the user to position the medicament delivery device 11 relative to the camera so that recordings of the medicament delivery device 11 may be captured, since the position of the camera relative to the medicament delivery device 11 may be adjusted with ease.

An example method of collecting medicament dosage information using the data collection apparatus 2 will now be described with reference to FIG. 5. In this particular example, the data collection apparatus 2 is a cellphone 20, as shown in FIG. 3, that is executing an app, and the camera 21 is capable of setting exposure and focus parameters automatically when capturing recordings.

Figure 5:
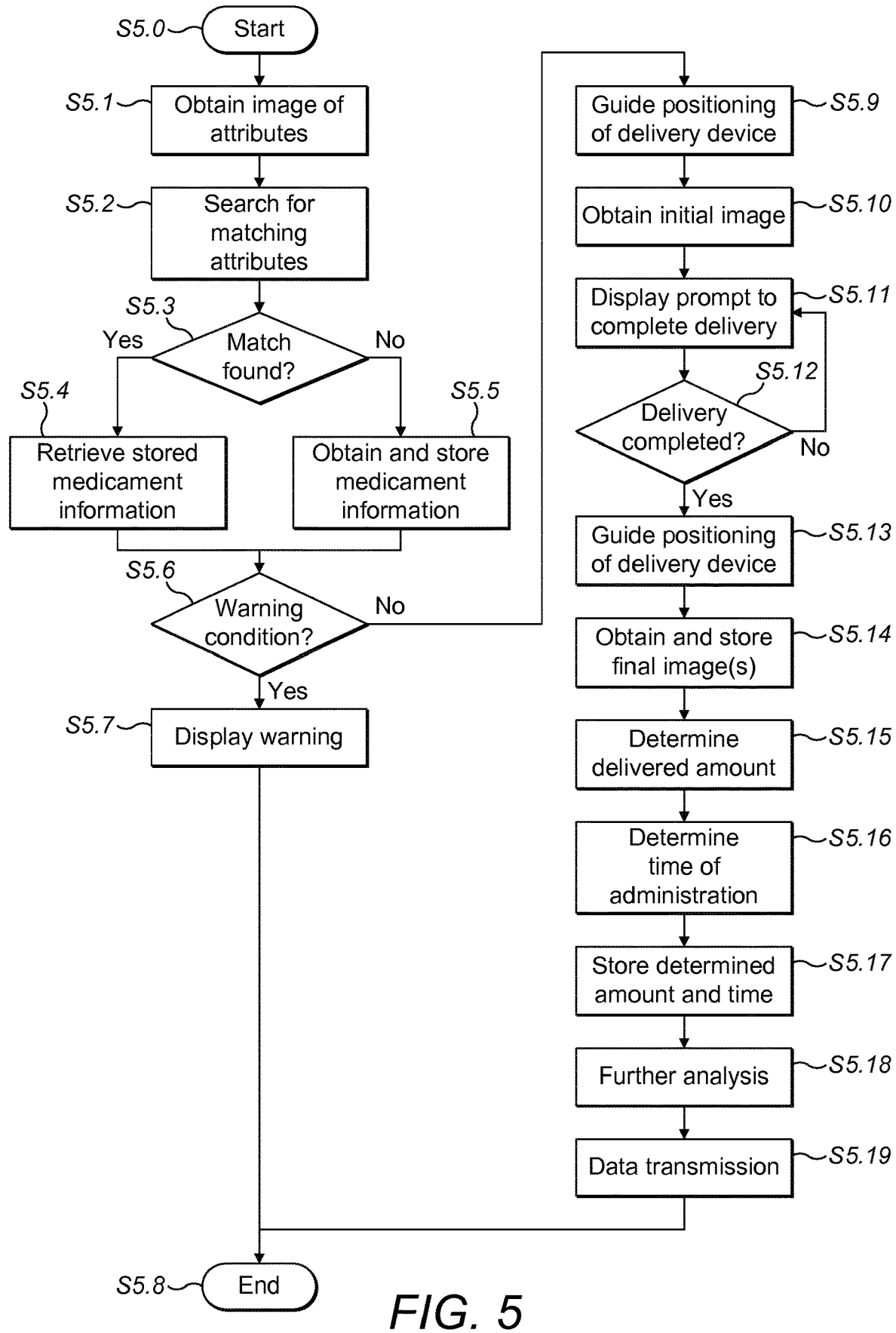
FIG. 5 is a flowchart of a data collection method according to an embodiment of the invention.

Starting at FIG. 5, the camera 21 is controlled by the app to obtain one or more recordings of at least a part of the medication delivery device 11 that includes some or all of the one or more visual attributes 18a, 18b, 18c (step s5.1). As noted above, the recording may be captured as a still recording or be part of a video.

The processing arrangement 22 then attempts to identify the medication delivery device 11 by searching for a match for some or all of the visual attributes 18a, 18b, 18c amongst reference visual attributes stored in the memory units 23, 24 (step s5.2), using pattern matching, feature recognition or another suitable analysis technique. For example, the reference visual attributes 18a, 18b, 18c be include attributes provided on particular models of the medical delivery devices 1 or may correspond to a type of medicament. Alternatively, or additionally, the reference attributes may include visual attributes of medicament delivery devices previously used by the user to administer injections.

If a match is found (step s5.3), then information regarding the medicament within the medicament delivery device 11 is retrieved from the memory units 23, 24 (step s5.4).

If a match is not found (step s5.3), then the processing arrangement 22 obtains and stores medicament information in the memory units 23, 24 (step s5.5). For instance, where the visual attributes 18a, 18b, 18c indicate medicament information, the processing arrangement 22 may analyse the recording of the visual attributes 18a, 18b, 18c to obtain the medicament information. Alternatively, or additionally, the processing arrangement 22 may output a request through the output arrangement 29, 30 for the user to input details of the medicament and/or medical delivery device 11, for example, via the input arrangement 27, 28.

The medicament information may also include information regarding a scale provided on the container 15 used to indicate the amount of medicament in the container 15 and/or parameters for use in parallax correction of recordings of the medicament delivery device 11.

In some implementations, the processing arrangement 22 is capable of determining whether a warning condition exists (step s5.6). For example, a warning condition may exist where the medicament delivery device 11 corresponding to the attributes 18a, 18b, 18c does not match a medicament delivery device 11 or a type of medicament delivery device 11 used previously by the user. Such a warning condition may be an indication that the user is attempting to administer an injection using another patient's medicament delivery device, or a medicament delivery device 11 that contains the wrong medicament or a medicament at the wrong concentration.

Another example of a warning condition that may be detected at step s5.6 relates to whether an expiry date for the medicament has passed. Such a determination may be based on the medicament information retrieved from the memory units 23, 24 at step s5.4 or obtained from the user or from analysis of the recording of the visual attributes 18a, 18b, 18c at step s5.5.

If it is determined that a warning condition exists (step s5.6), then a warning message may be presented to the user (step s5.7), for example using the display 29, and the process ends (step s5.8).

If no warning conditions are detected (step s5.6), or if step s5.6 is omitted, then the user is guided to position the medicament delivery device 11 to allow a recording of the chamber 14 to be captured by the camera 21 (step s5.9). An example guiding procedure will now be described with reference to FIGS. 6 and 7.

Starting at step s6.0, further recordings of the medicament delivery device 11 are captured, for example, as a video, and presented on the display 29 as a "live view" as a guide for the user to position the piston 17 in a particular region of a field of view of the camera 21 (step s6.1).

Figure 7:
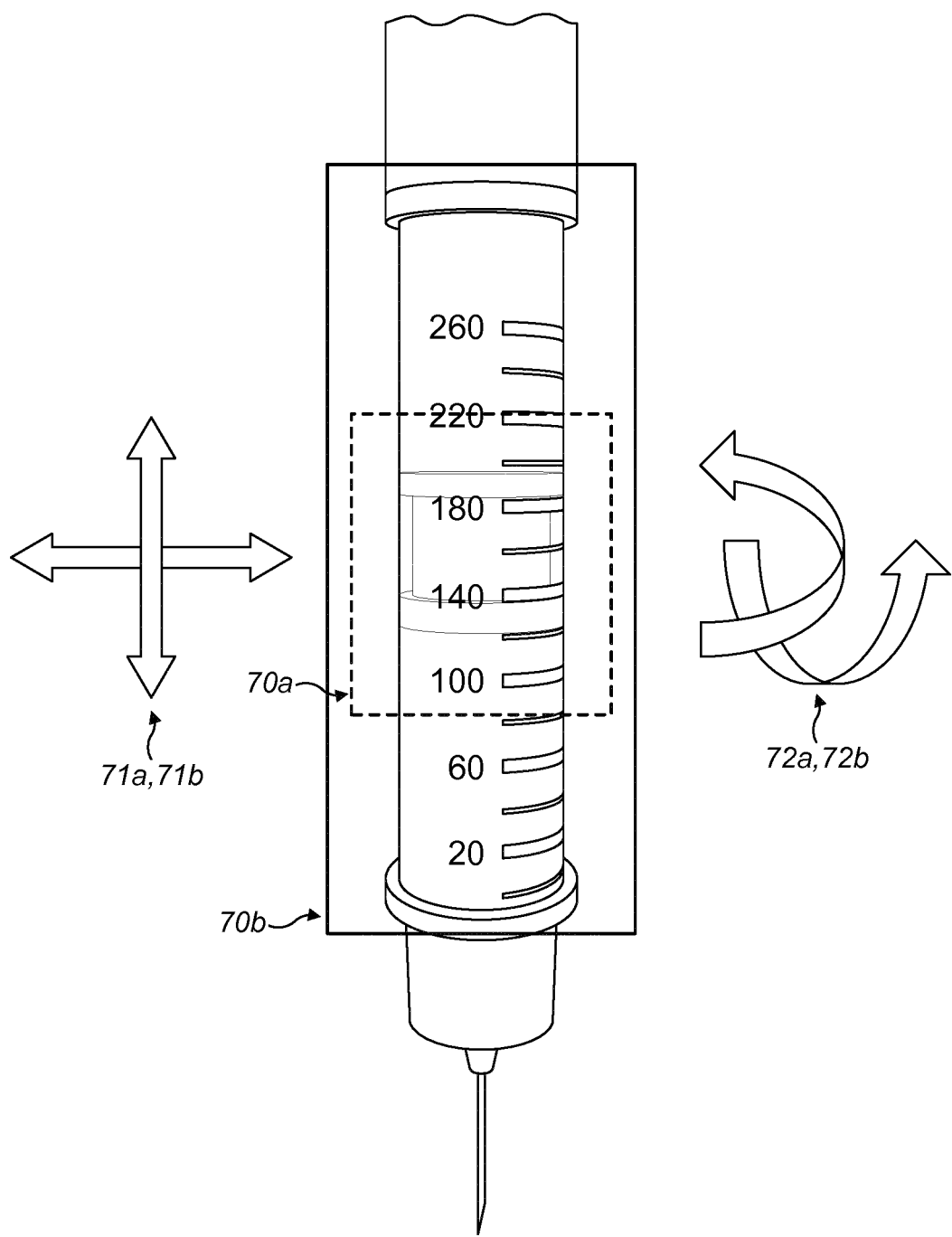
FIG. 7 depicts an example of a "live view" display in the guiding procedure of FIG. 6.

An example of a live view display is shown in FIG. 7. In this particular example, windows 70a, 70b are superimposed over the captured video recordings, each of which indicates a region of interest (ROI) in the recordings. The user can position the medicament delivery device 11 so that the recording of the piston 17 is located within the window 70a and at least a portion of a scale provided on the medicament container 15 is located within a larger window 70b. By causing the user to position the medicament delivery device 11 so that the piston 17 and scale are not close to the edges of the recording, the effects of distortion and/or vignetting from a lens of the camera 21 may be reduced or even avoided.

The processing arrangement 22 may determine, from the captured recordings, whether adjustments to the position of the medical delivery device 11 relative to the camera 21 are required so that the piston 17 and scale appear in their respective ROIs (step s6.2). To reduce computing resource requirements, the processing arrangement 22 may disregard edges of the recordings when determining the adjustments. For example, the app may be configured to process and analyse recording data from the ROIs and, optionally, the immediate surroundings of the ROIs.

Required translation adjustments may be determined at step s6.3 using feature recognition to identify the piston 17 and, optionally, edges of the housing 10 or tick marks on the medicament container 15 and then to determine the translation adjustments needed to position the piston 17 within the ROI based on the locations of the recognised features in the recording.

Some examples of suitable techniques for determining required tilt adjustments at step s6.3 will now be described.

Figure 8:
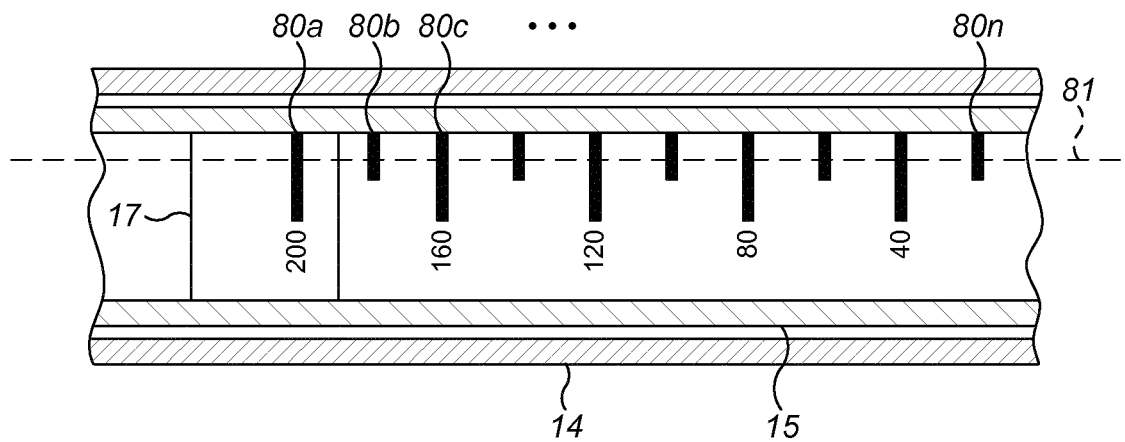
FIG. 8 depicts a recording of the medicament chamber of FIG. 2, showing examples of segments of the recording that may be used to determine whether the medicament delivery device is tilted relative to the data collection device.

FIG. 8 shows a recording of tick marks 80a to 80n, on the medicament container 15. The dashed line 81 in FIG. 8 indicates a sample of the recording pixels extending along a longitudinal axis of the chamber 14 with a thickness of, for example, 10 pixels. The variation in brightness of recording pixels along that line 81 is then determined. Where the tick marks 80a to 80n are regularly spaced, regular variations in the brightness along the line corresponding to the presence or absence of a tick mark would be expected, with the possible exception of the tick marks that overlie the position of the piston 17. In this particular example, a smoothed derivative of the brightness is used to determine whether the tick marks in the recording are regularly spaced and, therefore, whether the medicament delivery device 11 is tilted towards, or away from, the camera 21.

In another example technique, the processing arrangement 22 may perform contour tracking to detect short edges of some or all of the tick marks 80a to 80n, locate the centre of each of the tracked tick marks and determine whether those tick marks have their expected spacing. For regularly spaced tick marks, a relationship between the successive marks and their position along the container 15 that is linear within a required precision range would be expected.

Deviations from a linear relationship may indicate tilt, but may also be used to determine curvature of the scale denoted by the tick marks 80a to 80n, for use in correcting for parallax in the recording and effects of refraction of light passing through the walls of the chamber 14 and the container 15, which may distort the recording.

Figure 9A:
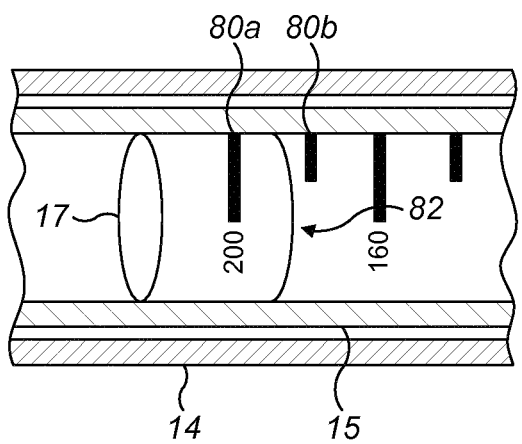
FIG. 9a depicts part of an recording showing a base of a piston in the medicament chamber when the medicament delivery device of FIG. 1 is positioned appropriately with respect to a camera.
Figure 9B:
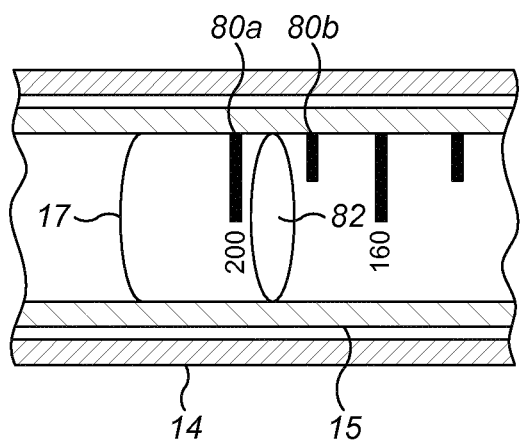
FIG. 9b depicts part of an recording showing the base of the piston when the medicament delivery device of FIG. 1 is tilted towards the camera.
Figure 9C:
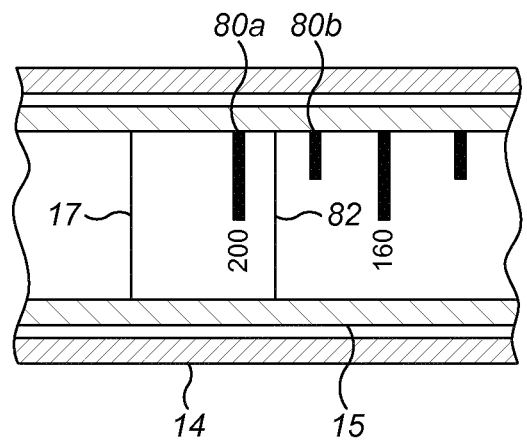
FIG. 9c depicts part of an recording showing the base of the piston when the medicament delivery device of FIG. 1 is tilted away from the camera.

A third technique for detecting tilt is based on a shape of a base 82 of the piston 17 as it appears in the captured recordings. By detecting curvature of an edge of the base 82 in the recording, the processing arrangement 22 may determine whether a tilt adjustment is needed. FIGS. 9a and 9b depict a recording of the piston 17 as having a curved edge when the base 82 is tilted away from the camera 21 and towards the camera 21 respectively. FIG. 9c depicts the recording of the piston 17 as having a straight edge when the base 82 is not tilted. However, the determination of the shape of the base 82 may include allowances for parallax and for burling on the piston base 82, which may cause the edge of the piston 17 to appear curved even when the base 82 is not tilted.

The app may then control the processing arrangement 22 to present movement indicators 71a, 71b, 72a, 72b in the live view display to guide the user's adjustments to the position of the medicament delivery device 11 (step s6.4). The movement indicators may include translation indicators 71a, 71b indicating how the medicament delivery device 11 should be translated relative to the camera 21 and/or tilt indicators 72a, 72b showing how the medicament delivery device 11 should be tilted relative to the camera 21. Where the data collection apparatus 2 has a built-in gyroscope or accelerometer, the output from those sensors may be also utilised in determining what movement is required. For example, the user may be guided to adjust the orientation and position of the camera 21, rather than the medicament delivery device 11.

The live view display may also be configured to guide the user to position the camera 21 at a distance at which the camera 21 can obtain a good focus on the dosage window 13. In certain embodiments, such focus may be achieved when the distance between the camera 21 and the medicament delivery device 11 is approximately 30 cm. In other embodiments, for example, where the camera 21 is operated in a "macro" mode, a good focus may be achieved when the camera 21 and the medicament delivery device 11 are separated by a smaller distance, such as approximately 7 cm.

Steps s6.1 to s6.4 are repeated until it is determined that no further adjustments to the position of the medicament delivery device 11 relative to the camera 21 are required (step s6.2) and the guiding procedure then ends (step s6.6).

Returning to FIG. 5, an initial recording is obtained and stored with a time stamp to record a start position of the piston 17 (step s5.10). As noted above, the camera 21 may be configured to capture video, in which case obtaining the initial recording may include selecting a recording from a sequence of recordings in a video.

Figure 6:
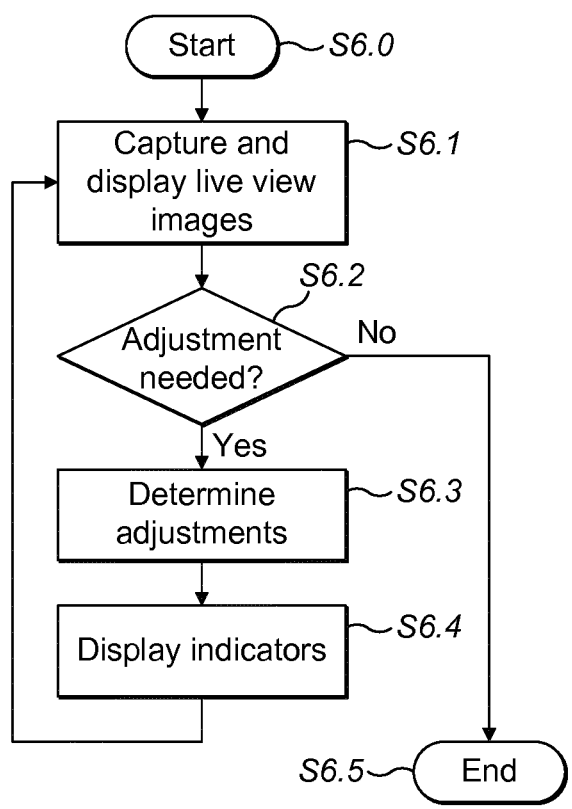
FIG. 6 is a flowchart of a guiding procedure in the method of FIG. 5.

The obtaining of the initial recording may be triggered automatically, in response to a determination by the processing arrangement 22 that the medicament delivery device 11 has been positioned suitably, at step s6.2 of the guiding procedure of FIG. 6. For example, recording capture may be triggered when it is determined that a good focus has been achieved and the position and orientation of the medicament delivery device 11 is determined to be within tolerable limits. In another example embodiment, the app causes the processing arrangement 22 to perform a feature detection algorithm, for example on the tick marks 80a to 80n and/or visual attributes 18c included in the recording and compares descriptors of the detected features with a reference recording for the same model of medicament delivery device, stored in the memory units 23, 24, to determine when the medicament delivery device 11 is correctly positioned and to trigger capture of the initial recording.

In an embodiment where the camera 21 captures a video, the initial recording may be obtained by capturing a sequence of video recordings and selecting a recording from that sequence. The selection may be triggered automatically, when it is determined by the processing arrangement 22 that the medicament delivery device 11 is suitably positioned and orientated and, optionally, a good focus has been achieved, in a similar manner to that described immediately above.

As noted above, the camera 21 may set exposure and focus parameters automatically. The camera 21 may be configured to set the exposure parameters to achieve a suitable contrast level, for example, to provide a contrast between the brightness of the brightest and darkest parts of the recording to at least 20%.

In some implementations where still recordings are used, the camera 21 may be controlled to take multiple recordings of the medicament device 11 with different exposure times and the processing arrangement 22 configured to combine the multiple recordings to provide a high dynamic range ("HDR") recording.

The processing arrangement 22 may perform pre-processing of the initial recording to assess and, if required, improve recording data quality by correcting for one or more of light conditions, distortion and jitter. For example, an exposure control algorithm in the app may reject pictures that are too bright, too dark or lack sufficient contrast and cause a new initial recording with adjusted exposure parameters to be captured automatically. In some implementations, the app may be designed to perform data collection without pre-processing of the recording.

Once a suitable recording of the medicament container 15 and piston 17 has been obtained (step s5.10), the app may prompt the user to administer the injection (step s5.11), for example by displaying a message on the display 29 and/or outputting an audio signal through the speaker 30 requesting the user to confirm via the input arrangement 27, 28 when the delivery has been completed.

The app then waits for an indication from the user confirming that medicament delivery is complete (step s5.12).

If a response from the user is received (step s5.12), then the user is guided to position the medicament delivery device 11 correctly with respect to the camera (step s5.13). In this particular example, the guiding procedure shown in FIG. 6 is used.

A final recording of the medicament container 15 and piston 17 is then obtained, and stored with a time stamp (step s5.14) to record the position of the piston 17 after the medicament has been delivered.

As described above in relation to the initial recording, the final recording may also be preprocessed before the position of the piston 17 in the final recording is determined.

The final recording may be a still recording captured by the camera 21. Where the camera 21 is configured to record video, one or more final recordings may be obtained at step s5.14 by performed by selecting one or more final recordings from the video. Where such multiple final recordings are selected, they may be processed and analyzed statistically to determine the position of the piston 17.

To determine the medicament dosage amount expelled from the container 15 (step s5.15), the position of the piston 17 shown in the initial recording, obtained at step s5.8 is compared with the position of the piston 17 in the final recording or determined from multiple final recordings obtained at step s5.14, in relation to the tick marks 80*a* to 80*n* shown in those recordings. In some implementations, the resolution of the initial and final recordings may be improved using averaging and/or interpolation.

Figure 10:
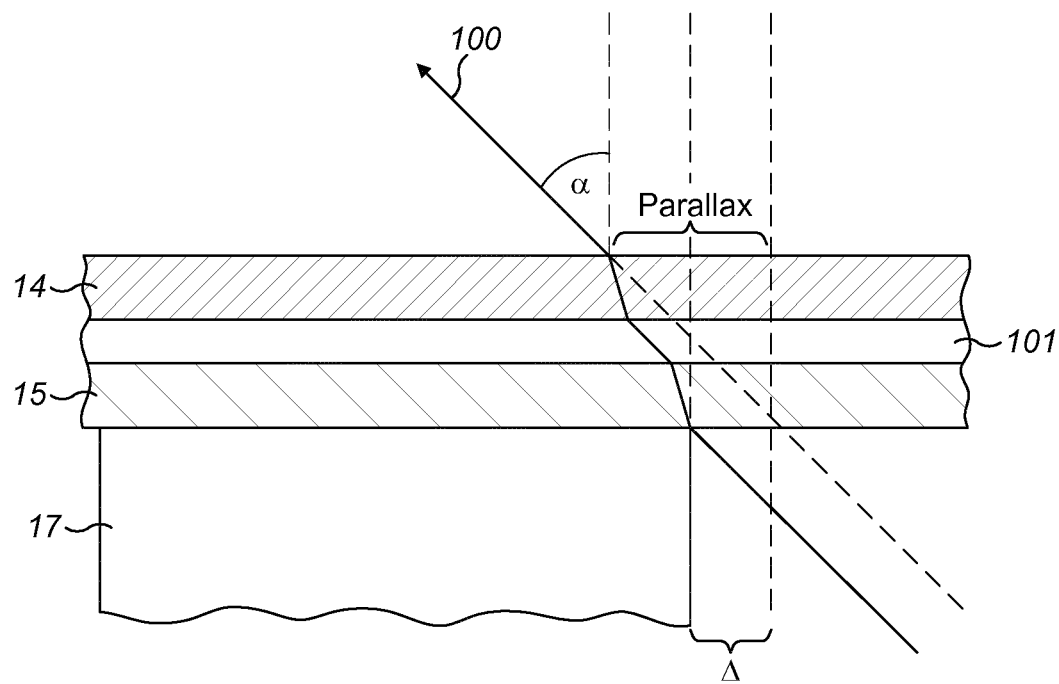
FIG. 10 is a diagram showing parallax and displacement of light rays passing through part of the chamber.

Also, as noted above, the resolution of the recording of the piston 17 will be reduced due to parallax and light refraction. FIG. 10 shows a light ray 100 passing through a portion of the container 15, air gap 101 and chamber 14 and the apparent displacement A shown in the captured recordings.

The apparent displacement A may be calculated by Equation (1):

$$\Delta = (d_1 + d_2)\tan(\alpha) - \left( \frac{d_1}{\sqrt{n_1^2 - \sin^2(\alpha)}} + \frac{d_2}{\sqrt{n_2^2 - \sin^2(\alpha)}} \right)\sin(\alpha) \quad (1)$$

where $d_1$ is the thickness of the wall of the chamber 14, $d_2$ is the thickness of the wall of the container 15, $n_1$ is the refractive index of the wall of the chamber 14, $n_2$ is the refractive index of the wall of the container 15 and $\alpha$ is an angle at which the light ray 100 leaves the wall of the chamber 14 with respect to the direction towards the camera 21.

Hence, a correction applied to the determined position of the base 82 of the piston 17 to account for parallax and refraction will vary according to the distance of the base 82 from the centre of the ROI in the initial and final recordings.

For an example medicament delivery device 11 in which the wall of the chamber 14 is polycarbonate and the wall of the container 15 is glass, the thicknesses $d_1$, $d_2$ of the walls of the chamber 14 and container 15 are 0.75 mm, and the refractive indices $n_1$, $n_2$ are 1.5. In a recording taken at a distance of 7 cm from the medicament delivery device 11, with a scale of 4 cm, a light ray exiting the wall of the chamber 14 at an angle of 16° would appear to be displaced by 0.15 mm, and an appropriate correction may be important.

A time of administration of the medicament and, in some implementations, a duration of the injection, may also be determined based on the time stamps of the initial and final recordings (step s5.16).

The determined medicament dosage amount is then stored in the memory units 23, 24 together with a dated and time of administration and, in some implementations, a duration of the administration (step s5.17). In some implementations, the stored information may be linked to other information regarding the user's physical condition or activities. For instance, the user may have entered data regarding their food intake, physical activity, use of other medications, test results or severity of symptoms in to the cellphone 20 via the app. For example, where the user has diabetes, test results regarding blood glucose levels may be entered. In this manner, the app may compile a database in which the medicament dosage information is provided with associated context regarding the patient's condition, to facilitate monitoring and adaptation of their treatment.

In some implementations, the app may be configured to cause the processing arrangement 22 to perform further analyses (step s5.18) based on the initial recording and final recordings and/or medicament dosage amount information. For example, if the initial recording shows the piston 17 in a position corresponding to a full medicament container 15, the processing arrangement 22 may determine that the medicament delivery device 11 is a new, unused device being used for the first time. The app may then monitor the expiry date of the medicament delivery device 11 based on the date on which the initial and final recordings were taken, so that a warning can be presented to the user via the output arrangement 29, 30 when the expiry date becomes imminent.

In some implementations, if the final recording indicates that the medicament container 15 is almost empty, then a warning may be presented to the user via the output arrangement 29, 30.

In some implementations, further analysis that may be performed at step s5.18, where the duration of the administered injection has been calculated, to determine the type of injection. For example, before using injection device 11 for the first time, it may be important for the user to perform a so-called "prime shot" to remove air from container 15 and needle 16, for instance by selecting a small dosage amount and pressing injection button 11 while holding medicament delivery device 11 with the needle 16 upwards. A short duration of time between the initial and final recordings combined with a small determined medicament dosage amount may indicate that, instead of an injection being administered, a prime shot had been performed, and so this may be indicated in the stored information for the medicament dosage. Also, in some embodiments, the app may respond to the determination that a prime shot has occurred by returning to an earlier step in the procedure of FIG. 5, since such a prime shot would be expected to precede an injection. For example, the app may return to step s5.9 to guide the user to take a new initial recording. Alternatively, the app may return to step s5.11, to prompt the user to administer a subsequent injection, since the amount of medicament in the container 15 at the start of the subsequent injection is known from the analysis of the final recording obtained at step s5.14.

In some implementations, at step s5.18, the app may also calculate a medicament dosage amount for the next administration of medicament, based on the dosage history stored in the memory units 23, 24.

The processing arrangement 22 may then transmit the stored information and, in some implementations, context information provided by the user and/or the initial and final recordings to another device via a network, such as a cellphone network, personal area network or the Internet, using the communications equipment 25, 26 (step s5.19). For example, such data may be transmitted to a remote server, for example, for analysis by a medical professional at a remote location or for cloud storage.

The method then ends (step s5.8).

Although the method of FIG. 5 was described with reference to an embodiment in which the data collection apparatus 2 was a single device, such as a cellphone 20, in another embodiment, the data collection apparatus 2 may include multiple devices, such as the separate camera device, data processing device and interface device shown in FIG. 4.

Further, while the recordings were analysed and data processing performed by the cellphone 20 in the method of FIG. 5, in another embodiment, the recordings and timestamps may instead be transmitted to a remote device for processing. Messages for the user relating to expiry dates and/or calculated dosages may be transmitted to the data collection apparatus 2 for presentation to the user, based on data processing performed remotely.

In the embodiment described above, the position of the base 82 of the piston 17 was determined relative to tick marks 80a to 80n. In another embodiment, the position of the base 82 may be determined relative to another fixed marking or feature of the medicament delivery device 11, such as the visual attributes 18a, 18b, 18c. Moreover, in other embodiments, the position of another movable component of the medicament delivery device 11 may be monitored instead of the base 82 of the piston. For example, the medicament delivery device 11 may be configured so that the dosage knob 12 rotates as the injection button 11 is pressed. In such an example, the medicament dosage amount may be determined from initial and final recordings of the dosage knob 12.

Furthermore, while the method of FIG. 5 included obtaining and analysis of an initial recording and a final recording of the container 15, in another embodiment the data collection apparatus 2 may be configured to obtain only the final recording, and to retrieve stored information from a previous injection administered using the medicament delivery device 11 instead of capturing and analysing an initial recording.

As shown by the embodiments discussed above, the provision of an app or similar software product to obtain information regarding an injection, other medical treatment or the operation of other equipment may permit more accurate and/or reliable recording of such information using a device such as a cellphone 20 or other computing device that is commonly available. Since the embodiments described above do not require the manufacture and distribution of a dedicated device, they may, potentially, reduce the costs and complexity of providing recordal and/or monitoring of treatment or operations. Also, the user may already be very familiar with such devices and, therefore, already be comfortable with their handling and operation.

While the embodiments above have been described in relation to collecting data from an insulin injector pen, it is noted that embodiments of the invention may be used for other purposes, such as monitoring of injections of other medicaments or other medical processes such as infusions.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intra-vascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetra-specific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A method of collecting data from a medicament delivery device, the method comprising:
   obtaining first and second recordings of at least a portion of the medicament delivery device using a camera, said portion including a first component that moves relative to a second component of the medicament delivery device as medicament is expelled from the medicament delivery device, where each of the first and second recordings comprises at least one image or a series of images;
   determining, from said first and second recordings, positions in the first and second recordings of the first component relative to the second component; and
   determining an amount of a delivered dose of the medicament that has been expelled by the medicament delivery device by comparing the position in the first recording of the first component relative to the second component in the first recording with a position in the second recording of the first component relative to the second component in the second recording, the second recording having been captured at a different time than the first recording.

2. The method according to claim 1, wherein:
   said portion includes attributes indicating information relating to one or more of the medicament and the medicament delivery device, the method including determining said information based on said first recording.

3. The method according to claim 1, comprising:
   prior to obtaining the first recording, obtaining a preliminary recording using said camera;
   determining, based on said preliminary recording, whether the medicament delivery device is positioned to locate the first component in a particular region of a field of view of the camera with a predetermined orientation;
   if it is determined that the medicament delivery device is not positioned to locate the first component in said particular region with the predetermined orientation, determining one or more adjustments to be made to reposition the medicament delivery device relative to the camera; and
   displaying instructions to reposition the medicament delivery device relative to the camera based on the determined one or more adjustments.

4. The method according to claim 3, wherein capture of the first recording is triggered automatically in response to a determination that the medicament delivery device is positioned to locate the first component in said particular region with the predetermined orientation.

5. The method according to claim 3, wherein determining whether the medicament delivery device is positioned with the predetermined orientation comprises one or more of:
   analyzing a brightness profile of pixels in the preliminary recording;
   analyzing positions of features of the medicament delivery device in the preliminary recording; or
   analyzing shapes of features of the medicament delivery device in the preliminary recording.

6. The method according to claim 1, comprising:
receiving input information from a user relating to a medical condition and/or activities of the user; and
calculating a medicament dosage amount to be administered in a subsequent medicament delivery based on the determined delivered dosage amount and said input information.

7. A computer program comprising computer-readable instructions that, when executed by a processing arrangement, causes said processing arrangement to perform operations to:
obtain first and second recordings of at least a portion of a medicament delivery device using a camera, said portion including a first component that moves relative to a second component of the medicament delivery device as medicament is expelled from the medicament delivery device, where each of the first and second recordings comprises at least one image or a series of images;
determine, from said first and second recordings, positions in the first and second recordings of the first component relative to the second component; and
determine an amount of a delivered dose of the medicament that has been expelled by the medicament delivery device by comparing the position in the first recording of the first component relative to the second component in the first recording with a position in the second recording of the first component relative to the second component in the second recording, the second recording having been captured at a different time than the first recording.

8. The computer program according to claim 7, wherein a smartphone app comprises the computer program.

9. The computer program according to claim 7, wherein the computer-readable instructions, when executed by a processing arrangement, causes said processing arrangement to further perform operations to:
prior to obtaining the first recording, obtain a preliminary recording using said camera;
determine, based on said preliminary recording, whether the medicament delivery device is positioned to locate the first component in a particular region of a field of view of the camera with a predetermined orientation;
if it is determined that the medicament delivery device is not positioned to locate the first component in said particular region with the predetermined orientation, determine one or more adjustments to be made to reposition the medicament delivery device relative to the camera; and
display instructions to reposition the medicament delivery device relative to the camera based on the determined one or more adjustments.

10. The computer program according to claim 9, wherein capture of the first recording is triggered automatically in response to a determination that the medicament delivery device is positioned to locate the first component in said particular region with the predetermined orientation.

11. The computer program according to claim 9, wherein determining whether the medicament delivery device is positioned with the predetermined orientation comprises one or more of:
analyzing a brightness profile of pixels in the preliminary recording;
analyzing positions of features of the medicament delivery device in the preliminary recording; or
analyzing shapes of features of the medicament delivery device in the preliminary recording.

12. The computer program according to claim 7, wherein:
said portion includes attributes indicating information relating to one or more of the medicament and the medicament delivery device, the operations including determining said information based on said first recording.

13. The computer program according to claim 7, wherein the computer-readable instructions, when executed by a processing arrangement, causes said processing arrangement to further perform operations to:
receive input information from a user relating to a medical condition and/or activities of the user; and
calculate a medicament dosage amount to be administered in a subsequent medicament delivery based on the determined delivered dosage amount and said input information.

14. A data collection apparatus, comprising:
a camera configured to obtain first and second recordings of at least a portion of a medicament delivery device, said portion including a first component and a second component, the first component being configured to move relative to the second component as medicament is expelled from the medicament delivery device, where each of the first and second recordings comprises at least one image or a series of images; and
a processing arrangement configured:
to determine, from said first and second recordings, positions in the first and second recordings of the first component relative to the second component, and
to determine an amount of a delivered dose of the medicament that has been expelled by the medicament delivery device by comparing the position in the first recording of the first component relative to the second component in the first recording with a position in the second recording of the first component relative to the second component in the second recording, the second recording having been captured at a different time than the first recording.

15. The apparatus according to claim 14, further comprising an output arrangement, the apparatus being configured to:
prior to obtaining the first recording, obtain a preliminary recording using said camera;
using said processing arrangement, determine whether the medicament delivery device is positioned to locate the first component in a particular region of a field of view of the camera with a predetermined orientation based on the preliminary recording, if it is determined that the medicament delivery device is not positioned to locate the first component in said particular region with the predetermined orientation, determine one or more adjustments to be made to reposition of the medical delivery device relative to the camera; and
using the output arrangement, present instructions to reposition the medicament delivery device relative to the camera based on the determined one or more adjustments.

16. The apparatus according to claim 15, wherein the processing arrangement is configured to trigger the camera to capture the first recording in response to a determination that the medicament delivery device is positioned to locate the first component in said particular region with the predetermined orientation.

17. The apparatus according to claim 15, wherein, the processing arrangement is configured to determine whether the medicament delivery device is positioned with the predetermined orientation by being configured to:
- analyze a brightness profile of pixels in the preliminary recording;
- analyze positions of features of the medicament delivery device in the preliminary recording; and
- analyze shapes of features of the medicament delivery device in the preliminary recording.

18. The apparatus according to claim 14, further comprising:
- an input arrangement configured to receive input information from a user relating to a medical condition and/or activities of the user;
- wherein the processing arrangement is configured to calculate a medicament dosage amount to be administered in a subsequent medicament delivery based on the determined delivered dosage amount and said input information.

19. The apparatus according to claim 14, wherein said portion includes attributes indicating information relating to one or more of the medicament and the medicament delivery device, the apparatus being configured to determine said information based on said first recording.

20. The apparatus according to claim 14, wherein the apparatus is a smartphone.

* * * * *

UNITED STATES PATENT AND TRADEMARK OFFICE
CERTIFICATE OF CORRECTION

| | |
|---|---|
| PATENT NO. | : 11,504,480 B2 |
| APPLICATION NO. | : 16/468184 |
| DATED | : November 22, 2022 |
| INVENTOR(S) | : Michael Schabbach and Beate Franke |

It is certified that error appears in the above-identified patent and that said Letters Patent is hereby corrected as shown below:

On the Title Page

Under item "(73) Assignee:", delete "GMBH" and insert -- GMBH, Frankfurt am Main (DE) --

Signed and Sealed this
Tenth Day of January, 2023

*Katherine Kelly Vidal*

Katherine Kelly Vidal
*Director of the United States Patent and Trademark Office*